United States Patent
Namburi et al.

(10) Patent No.: US 6,663,897 B2
(45) Date of Patent: Dec. 16, 2003

(54) ORAL ITRACONAZOLE FORMULATIONS AND METHODS OF MAKING THE SAME

(75) Inventors: Ranga Raju Namburi, Greenville, NC (US); John Elgin Kerr, Winterville, NC (US)

(73) Assignee: DSM IP Assets B.V. (NL)

( * ) Notice: Subject to any disclaimer, the term of this patent is extended or adjusted under 35 U.S.C. 154(b) by 0 days.

(21) Appl. No.: 09/933,032

(22) Filed: Aug. 20, 2001

(65) Prior Publication Data

US 2002/0150620 A1 Oct. 17, 2002

Related U.S. Application Data

(60) Provisional application No. 60/266,653, filed on Feb. 6, 2001.

(51) Int. Cl.⁷ .......................... A61K 9/50; A61K 9/14; A61K 9/16; A61K 9/48; A61K 9/20

(52) U.S. Cl. ................. 424/490; 424/489; 424/497; 424/502; 424/494; 424/495; 424/464; 424/465; 424/451; 424/456; 424/439

(58) Field of Search ................ 424/489, 490, 424/497, 502, 494, 495, 464, 465, 456, 451, 439

(56) References Cited

U.S. PATENT DOCUMENTS

| | | | |
|---|---|---|---|
| 4,791,111 A | 12/1988 | Heeres et al. | |
| 5,633,015 A | 5/1997 | Gilis et al. | |
| 6,039,981 A | 3/2000 | Woo et al. | |
| 6,383,471 B1 * | 5/2002 | Chen et al. | |

FOREIGN PATENT DOCUMENTS

| | | | | |
|---|---|---|---|---|
| WO | 94/05263 | * | 3/1994 | ............ A61K/9/16 |
| WO | WO 94/16733 | | 8/1994 | |
| WO | WO 98/31360 | | 7/1998 | |
| WO | 98/42318 | * | 10/1998 | ............ A61K/9/50 |
| WO | 00/03697 | * | 1/2000 | |
| WO | WO 00/30616 | | 6/2000 | |
| WO | WO 00/56726 | | 9/2000 | |

OTHER PUBLICATIONS

*Organic Volatile Impurities*, USP24, p. 1877–1878 (no date).
*Celphere® Microcrystalline Cellulose Spheres*, FMC (1996).
Children's Health Environmental Coalition: HealtheHouse; Chemical Profile: dichloromethane; www.checnet.org/HealtheHouse (Oct. 21, 2002).
*Methylene Chloride, Agency for Toxic Substances and Disease Registry*, CAS #75–09–2 (Feb. 2001).

* cited by examiner

Primary Examiner—Thurman K. Page
Assistant Examiner—Humera N. Sheikh
(74) Attorney, Agent, or Firm—Myers Bigel Sibley & Sajovec

(57) ABSTRACT

A method of manufacturing an itraconazole oral dosage form that is substantially free of residual methylene chloride comprises the steps of: (a) providing a working solution comprising an alcohol, a strong acid (preferably an inorganic acid or organic sulphonic acid), itraconazole, a water-soluble polymer, and water, with the itraconazole and the strong acid preferably present in the working solution in a ratio of 1 Mole itraconazole to 1–3 Moles acid; (b) providing particles formed from a pharmaceutically acceptable core material; (c) combining the working solution with the particles to produce itraconazole-coated particles; (d) drying the itraconazole-coated particles; and (e) forming the dried itraconazole-coated particles into an itraconazole oral dosage form that is substantially free of residual methylene chloride. The products of such methods and methods of use thereof are also disclosed.

25 Claims, No Drawings

ORAL ITRACONAZOLE FORMULATIONS AND METHODS OF MAKING THE SAME

RELATED APPLICATIONS

This application claims the benefit of provisional application serial No. 60/266,653, filed Feb. 6, 2001, the disclosure of which is incorporated by reference herein in its entirety.

FIELD OF THE INVENTION

The present invention concerns methods of making oral itraconazole formulations, the oral dosage forms so made, and methods of use thereof.

BACKGROUND OF THE INVENTION

Itraconazole (also known as (±)-cis-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one) is a triazole antifungal compound with a piperazine portion. See generally Merck Index Reg. No. 5262 ($12^{th}$ ed. 1996). Itraconazole is disclosed in U.S. Pat. No. 4,267,179 to Heeres et al.

Itraconazole has an extremely low solubility in water. Indeed, its water and 0.1 N Hydrochloric acid solubilities are less than 1 microgram and 6 micrograms per milliliter respectively. Its pKa value is 3.7 and it remains largely un-ionized in human gastric secretions. Itraconazole is a classic example of a class 4 compound—one with low solubility and low permeability—based on the Biopharmaceutics Classification System and considerable effort has been devoted to developing oral formulations of itraconazole.

PCT Application WO 94/05263 to Gillis et al. (assigned to Janssen Pharmaceutica) describes 25–30 mesh beads having a core coated with itraconazole or saperconazole, which beads may be used to produce dosage forms of these drugs. To prepare the beads, the drug coating solution is dissolved into a suitable solvent system which is then combined with the beads. However, the only solvent system described is one comprising methylene chloride and an alcohol (see page 4, line 4 therein).

PCT Application WO 98/42318 to Vandecruys et al., (assigned to Janssen Pharmaceutica) describes 30–60 mesh beads having a core coated with itraconazole or saperconazole, which beads may likewise be used to produce dosage forms of these drugs. To prepare the beads the drug coating solution is, again, dissolved into a suitable solvent system. Again the only solvent system described is one comprising methylene chloride and an alcohol, and it is stated that the methylene chloride should comprise at least 50% by weight of the solvent system (see page 8, lines 32–34 therein).

Itraconazole is currently available as an oral formulation as SPORANOX™ itraconazole capsules. The capsules contain 100 mg of itraconazole coated on sugar spheres. See generally Physician's Desk Reference, page 1457 (54th ed. 2000). These capsules are currently believed to contain residual levels of methylene chloride and original SPORANOX® capsules were reformulated (per Summary Basis of Approval of the product) to the USP limit for methylene chloride which is 500 micrograms per day. See, e.g. USP 24 NF19, pages 1877–1878. Current SPORANOX® technology produces a product having approx. 60% less bioavailability under fasted conditions. See generally Physician's Desk Reference.

PCT Application WO 00/56726 to Erkoboni et al. (assigned to FMC Corp.) takes a different approach from the foregoing. Erkoboni describes a "hot melt" technique in which a normally solid hydrophobic vehicle is melted to dissolve itraconazole therein, and then the molten product granulated to produce granular particles that may be milled to appropriate size for the preparation of solid dosage forms. Structurally, the granular particles are solid solutions of the active agent rather than coated particles. A problem with hot melt procedures is the potential for thermal degradation of the active ingredient at elevated temperatures during manufacture. Operation of the granulator at higher temperatures, rapid cooling of the granulate, and discharging hot granulate through liquid nitrogen as described in the above patent requires special equipment for handling in the pharmaceutical industry. Dissolution testing of the itraconazole granulates thus made has shown only 51% dissolution of the drug in 60 minutes and thus offers no advantage for making an immediate release dosage form.

Accordingly, there remains a need for new ways to produce intraconazole oral dosage forms that utilize coated particles, but do not require the use of methylene chloride during the manufacture thereof.

SUMMARY OF THE INVENTION

A first aspect of the present invention is a method of manufacturing an itraconazole (or other water-soluble antifungal agent) oral dosage form that is substantially free of residual methylene chloride. The method comprises the steps of: (a) providing a working solution comprising or consisting essentially of an alcohol, a strong acid, itraconazole, a water-soluble polymer, and water, with the itraconazole and the strong acid preferably present in the working solution in a ratio of 1 Mole itraconazole to 1 or 1.2 to 2.5 or 3 Moles strong acid; (b) providing particles formed from a pharmaceutically acceptable core material; (c) combining the working solution with the particles to produce itraconazole-coated particles; (d) drying the itraconazole-coated particles; and (e) forming the dried itraconazole-coated particles into an itraconazole oral dosage form that is substantially free of residual methylene chloride (e.g., contains less than 200 ppm methylene chloride, less than 100 ppm methylene chloride, less than 50 ppm methylene chloride, less than 20 ppm methylene chloride, or even less than 10 ppm methylene chloride).

In one embodiment of the foregoing, the dried itraconazole-coated particles preferably comprise, by weight from 5 to 40 percent itraconazole; from 10 to 50 percent particle core material; and from 10 to 80 percent water-soluble polymer.

A second aspect of the present invention is a pharmaceutically acceptable particle comprising (a) a central rounded or spherical core comprised of a core material; and (b) a coating film formed on the core, the coating film comprising a water-soluble polymer and itraconazole. The particle preferably comprises, by weight, from 5 to 40 percent itraconazole; from 10 to 50 percent particle core material; and from 10 to 80 percent water-soluble polymer; and with the particle substantially free of methylene chloride (e.g., containing less than 200 ppm methylene chloride, less than 100 ppm methylene chloride, or even less than 50 ppm methylene chloride).

A third aspect of the present invention is an itraconazole oral dosage form that is substantially free of residual methylene chloride, the formulation comprising an effective antifungal amount of particles as described above. Typically, such a dosage form contains from 50 to 300 milligrams of itraconazole.

A further aspect of the present invention is a method of treating a fungal infection in a subject in need thereof, comprising orally administering to the subject an oral dosage form as described above in an antifungal-infective amount.

In a preferred embodiment of the foregoing, the stabilized formulation provides about ten fold increased solubility under pH 5.0 dissolution conditions and there by results in enhanced bio-availability of the active ingredient under fasted conditions. The in-situ salt formation of the active compound prevents its recrystallization from its acidic aqueous solutions.

The foregoing and other objects and aspects of the present invention is explained in greater detail in the specification set forth below.

Detailed Description of the Preferred Embodiments

Itraconazole as used herein is to be interpreted broadly and comprises the free base form and the pharmaceutically acceptable addition salts of itraconazole, or of one of its stereoisomers, or of a mixture of two or three of its stereoisomers. A preferred itraconazole compound is the (±)-(cis) form of the free base form and a mixture of four cis diastereo isomers. The acid addition forms may be obtained by reaction of the base form with an appropriate acid. Appropriate acids comprise, for example, inorganic acids such as hydrohalic acids, e.g., hydrochloric or hydrobromic acid; sulfuric acid; nitric acid; phosphoric acid and the like; or strong organic acids such as, for example, methanesulphonic, ethanesulphonic, benzenesulphonic, 4-methylbenzenesulphonic, cyclohexanesulfamic, and like acids. Itraconazole is known and may be produced in accordance with known techniques such as, for example, described in U.S. Pat. No. 4,916,134 (applicants specifically intend that the disclosures of all United States Patent references cited herein be incorporated herein in their entirety).

While the present invention is described herein with respect to itraconazole, those skilled in the art will appreciate that other sparingly water-soluble antifungal agents can be substituted for the itraconazole. Examples of such other antifungal agents include, but are not limited to, azoles such as saperconazole, ketoconazole, fluconazole, miconazole, etc.

Particles used herein may be of any suitable size, typically from about 100 to 1000 micrometers in diameter. Examples include particles with a diameter of about 600 to 250 um (30–60 mesh), or a diameter of 700 to 600 um (25–30 mesh). Size of particles can be determined in accordance with known techniques, such as described in the CRC Handbook, $64^{th}$ edition, page F-114 and USP24/NF19, page 1969.

Any suitable core material can be used for the particles. Examples of such materials are polymers e.g., plastic resins; inorganic substances, e.g., silica, glass, hydroxyapatite, salts (sodium or potassium chloride, calcium or magnesium carbonate) and the like; organid substances, e.g., activated carbon, acids (citric, fumaric, tartaric, ascorbic and the like acids), and saccharides and derivatives thereof. Particularly suitable materials are saccharides such as sugars, oligosaccharides, polysaccharides and their derivatives, for example, glucose, rhamnose, galactose, lactose, sucrose, mannitol, sorbitol, dextrin, maltodextrin, cellulose, microcrystalline cellulose, sodium carboxymethyl cellulose, starches (maize, rice, potato, wheat, tapioca) and the like saccharides.

Preferred as a core material for carrying out the present invention is microcrystalline cellulose particles or spheres, which can be produced in accordance with known techniques as described in U.S. Pat. Nos. 4,159,345; 4,149,346; 4,160,014; 4,196,219; 4,199,368; 4,231,802; 4,234,316; 4,275,196; 4,290,911; 4,319,975; 4,330,338; 4,381,082; 4,387,164; 4,415,428; 4,462,839; 4,484,141; 4,504,641; 4,518,433; 4,542,200; 4,588,555; 4,659,672; 4,689,302; 4,693,896; 4,695,548; 4,701,754; 4,717,667; 4,744,987; 4,749,620; 4,774,093; 4,861,448; 4,966,713; 4,983,268; 4,990,611; 5,051,261; 5,053,332; 5,075,115; 5,143,646; 5,155,144; 5,206,030; 5,212,299; 5,258,436; 5,277,915; 5,326,572; etc.

Currently preferred microcrystalline cellulose spheres are available as CELPHERE® spheres from Asahi Chemical Industry, Tokyo, Japan. Of these, CP-507 grade, 600 micrometer diameter CELPHERE® microcrystalline cellulose spheres are currently preferred.

The particles or spheres may optionally be protected with a barrier coating prior to formation of the itraconazole-containing film thereon, for example in the case where sugar is the core material and the barrier layer is provided to reduce caramelization, for stability and/or cosmetic purposes.

Any suitable water soluble polymer may be used herein. In one preferred embodiment the polymer has an apparent viscosity of 1 to 100 mPa.s when dissolved in a 2% aqueous solution at 20° C. solution. Examples of suitable water soluble polymers include, but are not limited to, alkylcelluloses such as methylcellulose, hydroxyalkylcelluloses such as hydroxymethylcellulose, hydroxyethylcellulose, hydroxypropylcellulose and hydroxybutylcellulose; hydroxyalkyl alkylcelluloses such as hydroxyethyl methylcellulose and hydroxypropyl methylcellulose; carboxyalkylcelluloses such as carboxymethylcellulose; alkali metal salts of carboxyalkylcelluloses such as sodium carboxymethylcellulose; carboxyalkylalkylcelluloses such as carboxymethylethylcellulose; carboxyalkylcellulose esters; starches; pectins such as sodium carboxymethylamylopectin; chitin derivatives such as chitosan; polysaccharides such as alginic acid, alkali metal and ammonium salts thereof, carrageenans, galactomannans, traganth, agar—agar, gum arabicum, guar gum and xanthan gum; polyacrylic acids and salts thereof; polymethacrylic acids and salts thereof, including methacrylate copolymers polyvinylpyrrolidone, copolymers of polyvinylpyrrolidone with vinyl acetate; polyalkylene oxides such as polyethylene oxide and polypropylene oxide and copolymers of ethylene oxide and propylene oxide; etc. Currently preferred is hydroxy propyl methyl cellulose, manufactured by Dow Chemical Industries, USA and also by Shin-Etsu Chemical Company, Japan.

Alcohols which may be used in the present invention include, but are not limited to, ethanol, particularly denatured ethanol such as SD3A alcohol. Other suitable alcohols include, but are not limited to, methanol, propanol (e.g., isopropyl alcohol), butanol such as tert-butyl, etc., including mixtures thereof. Currently preferred is SD3A alcohol, available from Van Waters & Rogers, Inc., 3600 Windover Avenue, Greensboro, N.C., USA 27407.

Strong acids that may be used to carry out the present invention may, in general, be inorganic acids or organic sulphonic acids. Examples of inorganic acids that may be used in the present invention include, but are not limited to, hydrochloric acid, sulfuric acid, phosphoric acid, nitric acid, hydrobromic acid, etc. Examples of organic sulphonic acids that may be used to carry out the present invention include, but are not limited, to methane sulphonic acid, ethane sulphonic acid (including derivatives thereof), benzene sulphonic acid, toluene sulphonic acid, naphthalene sulphonic acid, etc.

The coating film of the particles described herein may further comprise one or more pharmaceutically acceptable excipients such as, for example, plasticizers, flavors, pigments (e.g., titanium dioxide), preservatives and the like.

In addition, the particles according to the present invention may further contain one or more additional additives such as thickening agents, lubricants, surfactants, preservatives, complexing and chelating agents, electrolytes or other active ingredients, e.g., antiinflammatory agents, antibacterials, disinfectants or vitamins.

The pellets of the invention are prepared by dissolving into a solvent system of aqueous alcohol with varying proportions of alcohol and water and strong acid as described here in appropriate amounts of itraconazole and water-soluble polymer. The drug coating process may be conducted in a fluidized bed coater in accordance with known techniques. The spray rate in the FB coater should be regulated carefully to avoid spray drying of the drug coating solution, or over wetting with subsequent twin formation/agglomeration.

The pellets of the invention can be formulated into various pharmaceutical dosage forms, including capsules and tablets. In one embodiment, the pellets are filled into a hard gelatin capsule, sizes ranging from 1, 0, 0 elongated or 00. Tablets can be produced by conventional tabletting techniques with conventional ingredients or excipients. The tablets are preferably formed from a composition comprising the particles described herein distributed in a mixture of a disintegrant and a diluent or filler. Suitable disintegrants include, but are not limited to, crospovidone and croscarmellose. Suitable diluents include, but are not limited to, lactose, sucrose, dextrose, mannitol, sorbitol, starch, cellulose, calcium phosphate, microcrystalline celulose such as AVICEL®, etc. Tablets may include a variety of other conventional ingredients, such as binders, buffering agents, lubricants, glidants, thickening agents, sweetening agents, flavors, and pigments.

Subjects afflicted with a fungal infection that may be treated with the oral dosage forms described herein include both human subjects and animal subjects (particularly mammalian subjects such as dogs, cats and rabbits). Disorders with which such subjects may be afflicted include, blastomycosis (pulmonary and extrapulmonary), histoplasmosis (including chronic cavitary pulmonary disease and disseminated, non-meningeal histoplasmosis), aspergillosis (pulmonary and extrapulmonary) and onychomycosis (of the toenail and/or fingernail). The dosage of itraconazole will vary depending upon factors such as the disease and severity thereof, the age, weight and condition of the subject, etc., but in general is between 50 or 100 milligrams per day up to 800 or 1000 milligrams per day. The dosage form or forms may be administered to the subject at a single time or (more preferably) on multiple occasions over the day, and may be administered to the subjects under fed conditions (that is, simultaneously with food, or shortly before or after the subject has eaten so that the residence time of the dosage form in the subject's stomach is longer as compared to fasted conditions) or may be administered to the subject under fasted conditions (that is, without concurrent food administration so that the residence time of the dosage form in the subject's stomach is shorter as compared to fed conditions).

The present invention is explained in greater detail in the following non-limiting examples.

EXAMPLE 1

Preparation of Itraconazole Formulation

An itraconazole formulation of the present invention is prepared from the ingredients set forth in Table 1.

TABLE 1

Itraconazole and Hydrochloric Acid ratio is 1:1.6 Moles

| Name of Ingredient | Percent | Quantity |
| --- | --- | --- |
| Microcrystalline Cellulose Spheres (Celpheres)[1] | 36.28 | 1,500 g |
| Micronized Itraconazole | 18.86 | 780 g |
| Hydroxy Propyl Methyl Cellulose 5 cps | 42.45 | 1,755 g |
| Titanium Dioxide USP | 0.85 | 35.1 g |
| Hydrochloric Acid 37% NF/EP[2] | 1.56 | 174.5 g |
| Alcohol SD3A Anhydrous[3] | 0.0 | 28,070 g |
| Purified Water USP/EP[3] | 0.0 | 3,264 g |
| Total | 100.0 | 4,134.66 g |

[1]CP 507 grade Celpheres ® are used
[2]Supplied as 37% Hydrochloric Acid and contributes 64.56 g of total solids
[3]Removed in the process A 19.22 kg portion of SD3A alcohol was added to a stainless steel container. The hydroxypropyl methyl cellulose was added under stirring. When it forms a uniform suspension, the purified water was added under stirring. The stirring was continued until a translucent solution was formed. At the end of stirring, titanium dioxide was added and stirring continued for another ten minutes until a uniform suspension was formed.

Next, a 6.85 kg portion of SD3A alcohol was combined with the hydrochloric acid and stirred for ten minutes. To this solution, the itraconazole was added under stirring and the stirring continued for an additional fifteen minutes.

Next, the itraconazole solution was added to the hydroxypropyl methyl cellulose solution under stirring and stirring continued for 20 minutes. After stirring was completed the solution was homogenized for 2 minutes. The pH of the solution is then checked and a 2.0 kg portion of SD3A alcohol was added under impeller stirring. At this stage the weight of the solution is checked and adjusted accordingly with additional quantities of alcohol.

A Glatt GPCG-5 fluidized bed coater equipped with a Wurster spray insert is used for coating of the particles. Note that powder generation (spray drying) should be avoided and the filter bag placed properly to avoid losses. The spray rate is gradually increased from a starting rate of 15 grams to a final rate of 30 to 35 grams per minute towards the end of the process. Loading is performed at a temperature of 34–42° C. The coated particles are then dried for approximately 10–12 hours in a tray dryer at 45–50° C.

The coated particles described above are then used to fill a size 0, CAPSUGEL™ elongated hard gelatin capsule to provide a finished oral dosage having the ingredient weights and proportions as set forth below:

EXAMPLE 2

Dissolution Testing Methods

This test is provided to determine compliance with the dissolution requirements where stated for a tablet or capsule dosage form. Apparatus 2 as described in USP is used in the testing of Itraconazole 100 mg capsules and the conditions used are described below.

| | |
|---|---|
| Apparatus: | USP rotating paddle (Apparatus II) |
| Stirring Speed: | 100 rpm |
| Temperature: | 37° C. ± 0.5° C. |
| Sample Size: | Single weighted capsule |
| Medium: | 900 mL of deaerated 0.1 N Hydrochloric acid |

Medium Preparation: Add 83 mL of concentrated hydrochloric acid to 10 L of Milli-Q water and mix well.

Deaeration: For manual dissolution, (e.g. VanKel 7010 dissolution bath, VanKel Corporation) six liters of the medium is placed in a suitable glass vessel, and heated to 41° C. The medium is maintained at this temperature for 15 minutes. The medium is then vacuum filtered using a suitable filter (Millipore 0.45 μm type HPLV). For automated dissolution, (e.g. Zymark Multi-Dose system, Zymark Corporation) use 10 minutes of Helium sparging.

Sinker Preparation: A suitable capsule sinker is prepared by wrapping a 8 cm length of 316 stainless steel wire (32/1000ths diameter) around a glass Pasteur pipet to form a coil with approximately four turns.

Sample Preparation: Weigh each capsule prior to wrapping with the sinker, and record the weight. Drop a single weighted capsule into a suitable dissolution vessel containing 900 mL of medium under the conditions listed above. A total of six capsules are tested at the same time. Withdraw a measured aliquot, (not to exceed 10 mL) of the dissolution medium at 60 minutes for a single point, and 30 and 60 minutes for a profile. Filter the sample immediately through a syringe filter containing a 1 micron glass fiber membrane (Gelman Acrodisc 25 mm Syringe Filter part number 4523T), discarding the first portion of the filtrate. Transfer a portion of the sample into a suitable HPLC vial, and inject onto a suitable HPLC system.

Standard Preparation: Transfer approximately 100 mg, accurately weighed, of Itraconazole Reference Standard into a 900 mL volumetric flask. Dissolve the standard using 7.5 mL of concentrated hydrochloric acid. Swirl the acid gently until the standard is dissolved. Dilute to volume using Milli-Q water.

| HPLC Instrumental Conditions: | |
|---|---|
| Mobile Phase: | 65% Acetonitrile and 35% pH 7.0 Sodium Phosphate Buffer |
| Flow: | 2 mL/min |
| Injection Volume: | 10 μL |
| Column: | Agilent Technologies Eclipse XDB-C18 Rapid Resolution 3.5 μM 4.6 × 150 mm |
| Column Temp: | 40° C. |
| Detection: | UV at 254 nm |
| Runtime: | 5 minutes |

Note: All glassware is Class A grade. All chemicals are HPLC grade or equivalent. Milli-Q water refers to water of ultra high purity produced by passing steam distilled water through a Milli-Q water purification system manufactured by Millipore Corporation. The water produced from this system is consistently above 18 meg ohm in resistance.

Calculation $$\frac{\text{Sample area}}{\text{Average Standard area}} * \frac{\text{STD wt.}}{\text{SPL wt.}} * 100$$

The sample (SPL) weight is determined by subtracting 100 mg (average capsule shell weight) from the weight of the capsule sample. Multiply this result by the itraconazole %w/w contained in the formulation.

Itraconazole-coated particles prepared as described in Example 1 above were subjected to the dissolution test described in Example 2 above. Particles from commercially-available SPORANOX® capsules were subjected to the same test. The results are set forth in Table 2 below. Note the similar dissolution rates for the SPORANOX® particles and the particles prepared as described in Example 1 above.

TABLE 2

Dissolution Test Results in Simulated Gastric Fluid (pH 1.2)

| Product Details | | Minimum | Maximum | Average | Std. Dev. | % RSD |
|---|---|---|---|---|---|---|
| Example 1 Capsules | % Dissolved in 30 minutes | 83.3 | 91.0 | 87.0 | 3.7 | 4.3 |
| | % Dissolved in 60 minutes | 94.9 | 102.6 | 97.7 | 3.0 | 3.1 |
| | % Dissolved in 720 minutes | 102.0 | 103.1 | 102.7 | 0.5 | 0.5 |
| Sporanox Capsules | % Dissolved in 30 minutes | 47.7 | 79.2 | 59.4 | — | — |
| | % Dissolved in 60 minutes | 71.2 | 98.7 | 82.0 | — | — |
| | % Dissolved in 720 minutes | 86.4 | 102.8 | 96.6 | — | — |

EXAMPLE 3

Dissolution Test Results in pH 5.0 Phosphate Buffer

The test described in Example 2 was repeated, except a 50 mM pH 5.0 phosphate buffer was used as a direct replacement for the 0.1 N HCl media to represent a subject's stomach contents under fasted conditions. It was prepared by transferring approximately 42.6 grams of anhydrous sodium phosphate dibasic into a 6 liter flask containing 6 liters of Milli-Q water. The solution was stirred using a magnetic stir bar until the salt dissolved completely. The solution was pH adjusted to 5.0 using drop wise addition of concentrated phosphoric acid. The solution was sparged using helium for 10 minutes before use to remove trapped air from the solution.

Results are set forth in Table 3 below. Note the much higher dissolution rates for the particles prepared as described in Example 1, as compared to the dissolution rates for the commercial SPORANOX® particles. This indicates that the particles prepared as described in Example 1 should provide better drug delivery when administered to a patient under fasted conditions (who has not eaten food to stimulate gastric secretions and lower the stomach pH), as compared to the commercial SPORANOX® capsules.

TABLE 3

Dissolution Data in pH 5.0 Phosphate Buffer.

| Product Details | | Minimum | Maximum | Average | Std. Dev. | % RSD |
|---|---|---|---|---|---|---|
| Example 1 Capsules | % Dissolved in 30 minutes | 28.4 | 40.5 | 33.7 | 5.0 | 14.8 |
| | % Dissolved in 60 minutes | 56.1 | 64.1 | 61.0 | 3.6 | 5.9 |
| | % Dissolved in 720 minutes | 51.3 | 53.2 | 52.3 | 0.8 | 1.5 |
| Sporanox Capsules | % Dissolved in 30 minutes | 2.7 | 2.8 | 2.7 | — | — |
| | % Dissolved in 60 minutes | 5.7 | 6.8 | 6.3 | — | — |
| | % Dissolved in 720 minutes | 4.9 | 5.3 | 5.1 | — | — |

EXAMPLE 4

Stability Study

The batch samples prepared under Example 1 were evaluated for stability under accelerated conditions under ICH guidelines and three months stability results are furnished in Table 4.

Physical Examination Specification: Size 0 elongated hard gelatin capsule with an opaque white cap and a natural body. Capsules were substantially free from rough edges and spots and were filled with off white colored coated microcrystalline cellulose spheres.

The samples comply with the physical examination specifications at all time points.

Accelerated stability data indicates that there is no significant degradation of itraconazole and the dissolution profile is not affected by the stability conditions.

The foregoing is illustrative of the present invention, and is not to be construed as limiting thereof. The invention is defined by the following claims, with equivalents of the claims to be included therein.

and with said strong acid selected from the group consisting of inorganic acids and organic sulphonic acids;

providing particles formed from a pharmaceutically acceptable core material;

combining said working solution with said particles to produce itraconazole-coated particles;

drying said itraconazole-coated particles; and forming said dried itraconazole-coated particles into an itraconazole oral dosage form that is substantially free of residual methylene chloride.

2. A method according to claim 1, wherein said dried itraconazole-coated particles comprise, by weight:

from 5 to 40 percent itraconazole;

from 10 to 50 percent particle core material; and from 10 to 80 percent water-soluble polymer.

3. A method according to claim 1, wherein said strong acid is selected from the group consisting of hydrochloric acid, hydrobromic acid, nitric acid, sulfuric acid, and organic sulphonic acids.

4. A method according to claim 1, wherein said alcohol is selected from the group consisting of methanol, ethanol, propanol, butanol, and mixtures thereof.

5. A method according to claim 1, wherein said working solution further comprises a water soluble polymer selected from the group consisting of hydroxypropyl methylcellulose, methacrylate, hydroxypropylcellulose, and polyvinylpyrrolidones.

6. A method according to claim 1, wherein said working solution further comprises a pigment.

7. A method according to claim 1, wherein said working solution further comprises titanium dioxide.

8. A method according to claim 1, wherein said particles are microcrystalline cellulose spheres.

9. A method according to claim 1, wherein said particles are starch spheres.

10. A method according to claim 1, wherein said particles are from 100 to 1000 micrometers in diameter.

11. A pharmaceutically acceptable particle produced by the process of claim 1.

TABLE 4

Stability Results

| Time-point | Storage °C./% RH | Assay | Assay Total Impurities | Assay Unidentified (RRT 0.49) | Assay Triazole Impurity | Assay Unidentified 1 | Assay trans-Itraconazole | Assay Debutylated Itraconazole | Percent Dissolved in 60 minutes taking individual capsules |
|---|---|---|---|---|---|---|---|---|---|
| Initial | Initial | 102.1 | 0.22 | 0.00 | 0.06 | 0.08 | 0.02 | 0.06 | 100, 97, 93, 99, 85, 99, 101, 93, 89, 98, 105, 99 |
| 4 Week | 25/60 | 100.6 | 0.21 | 0.00 | 0.05 | 0.08 | 0.02 | 0.06 | 100, 104, 102, 106, 95, 100 |
| 12 Week | 25/60 | 102.1 | 0.19 | 0.00 | 0.05 | 0.07 | 0.00 | 0.07 | 100, 101, 96, 101, 85, 99 |
| 4 Week | 40/75 | 100.3 | 0.22 | 0.00 | 0.05 | 0.08 | 0.03 | 0.06 | 95, 102, 98, 101, 103, 104 |
| 8 Week | 40/75 | 100.9 | 0.36 | 0.14 | 0.04 | 0.10 | 0.03 | 0.05 | 101, 96, 101, 99, 99, 83 |
| 12 Week | 40/75 | 101.9 | 0.38 | 0.23 | 0.05 | 0.06 | 0.00 | 0.04 | 101, 100, 101, 105, 104, 96 |

That which is claimed is:

1. A method of manufacturing an itraconazole oral dosage form that is substantially free of residual methylene chloride, said method comprising the steps of:

providing a working solution consisting essentially of an alcohol, a strong acid, itraconazole, a water-soluble polymer, and water, with said itraconazole and said strong acid present in said working solution in a ratio of 1 Mole itraconazole to from 1 to 3 Moles strong acid, 12. The particle according to claim 11, wherein said core material comprises sugar.

13. The particle according to claim 11, wherein said core material comprises microcrystalline cellulose.

14. The particle according to claim 5, wherein said water soluble polymer is selected from the group consisting of hydroxypropyl methylcellulose, methacrylate, hydroxypropylcellulose, and polyvidones.

15. The particle according to claim 11, wherein said particle is from 100 to 1000 micrometers in diameter.

16. The particle according to claim 11, wherein said coating further comprises a pigment.

17. The particle according to claim 11, wherein said coating further comprises titanium dioxide.

18. An itraconazole oral dosage form comprising an effective antifungal amount of particles according to claim 11.

19. The dosage form according to claim 18, wherein said dosage form contains from 50 to 300 milligrams of itraconazole.

20. The dosage form according to claim 18, wherein said dosage form is a hard-gelatin capsule.

21. The dosage form according to claim 18, wherein said dosage form is a tablet.

22. A method of treating a fungal infection in a subject in need thereof, comprising orally administering to said subject an oral dosage form according to claim 18 in an antifungal-infective amount.

23. A method according to claim 22, wherein said oral dosage form is administered to said subject under fasted conditions.

24. A method according to claim 22, wherein said oral dosage form is administered to said subject under fasted conditions.

25. A method according to claim 22, wherein said subject is afflicted with blastomycosis, histoplasmosis, aspergillosis or onychomycosis.

* * * * *

UNITED STATES PATENT AND TRADEMARK OFFICE
CERTIFICATE OF CORRECTION

PATENT NO. : 6,663,897 B2
DATED : December 16, 2003
INVENTOR(S) : Namburi et al.

It is certified that error appears in the above-identified patent and that said Letters Patent is hereby corrected as shown below:

Column 12,
Line 6, should read
-- dosage form is administered to said subject under fed conditions. --

Signed and Sealed this

First Day of June, 2004

JON W. DUDAS
*Acting Director of the United States Patent and Trademark Office*